United States Patent [19]

Brogardh

[11] 4,342,919
[45] Aug. 3, 1982

[54] FIBER OPTICAL MEASURING DEVICE

[75] Inventor: Torgny Brogardh, Västerås, Sweden

[73] Assignee: ASEA Aktiebolag, Västerås, Sweden

[21] Appl. No.: 138,112

[22] Filed: Apr. 7, 1980

[30] Foreign Application Priority Data

Apr. 10, 1979 [SE] Sweden .................................. 7903175

[51] Int. Cl.³ .............................................. G01N 15/06
[52] U.S. Cl. .................................... 250/577; 73/293
[58] Field of Search .................... 250/577, 227; 73/293

[56] References Cited

U.S. PATENT DOCUMENTS 4,287,427  9/1981  Scifres ................................. 250/577

FOREIGN PATENT DOCUMENTS 319  1/1979  European Pat. Off. .

Primary Examiner—David C. Nelms
Assistant Examiner—Darwin R. Hostetter
Attorney, Agent, or Firm—Watson, Cole, Grindle & Watson

[57] ABSTRACT

The invention relates to a fiber optical measuring device for measuring physical parameters of a medium, preferably the level thereof, and it comprises an electronic unit and a transducer unit interconnected by an optical fiber, the transducer including at least one light guide connected to the optical fiber. The light guide is adapted to be lowered or introduced into the medium, the level, or other parameters, of which is to be measured, the light guide having a core with a higher refractive index than the surrounding sheath. The sheath has one or more regions along the light guide that are light transparent by being uncovered or only very thinly covered. When the guide is immersed into the medium, it influences the channel such that light in the thinly covered or uncovered regions of the guide is transmitted from the core, which light is representative of the level, or other parameter, of the medium.

16 Claims, 10 Drawing Figures

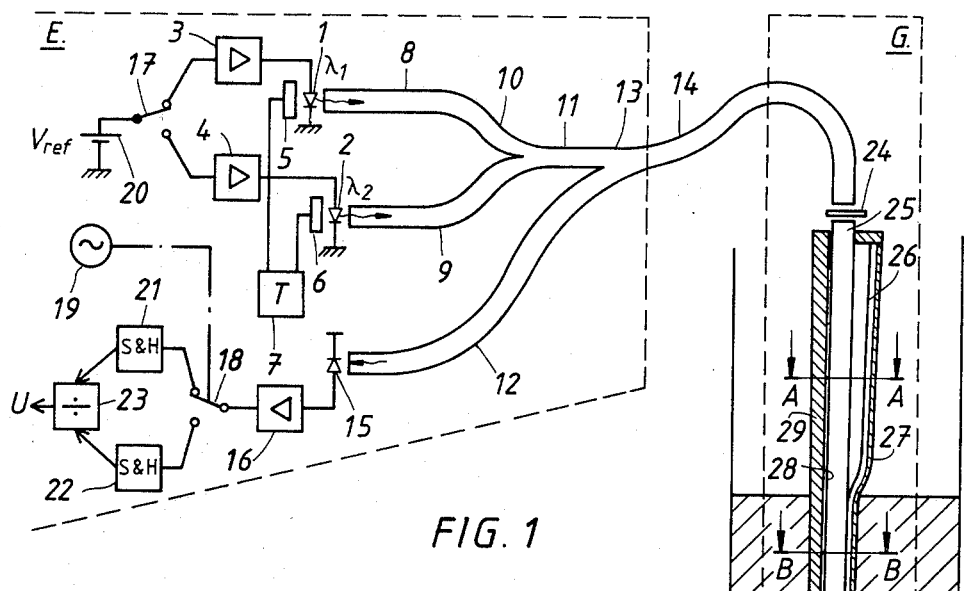
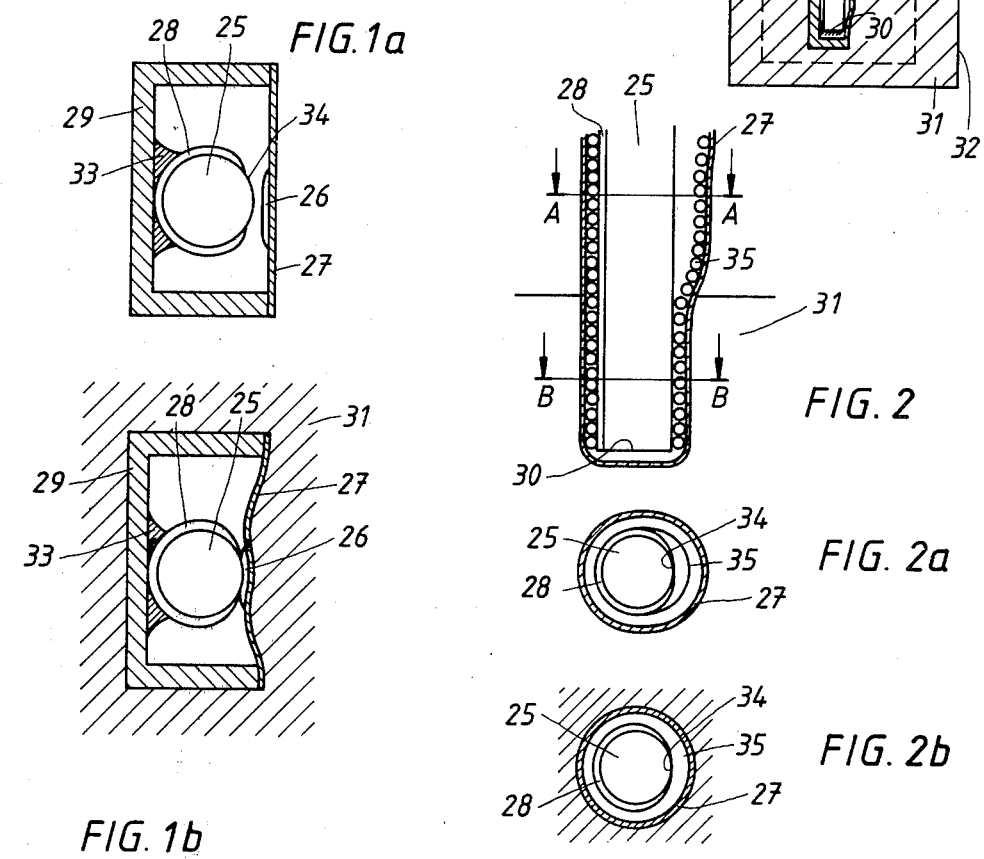

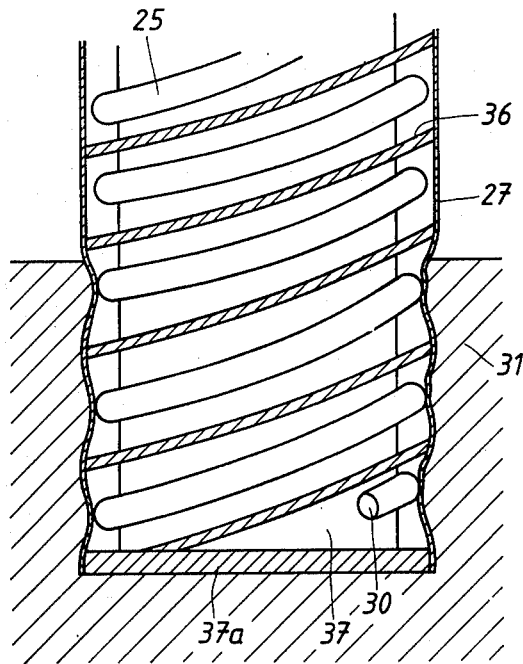
FIG.3
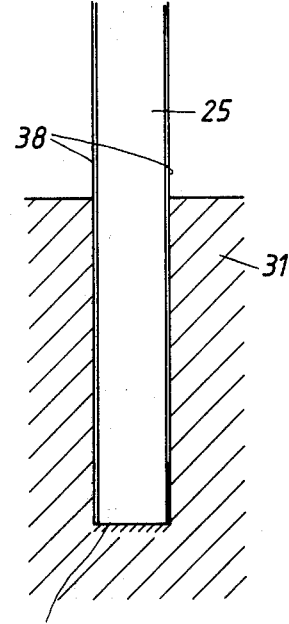
FIG.4
FIG.5
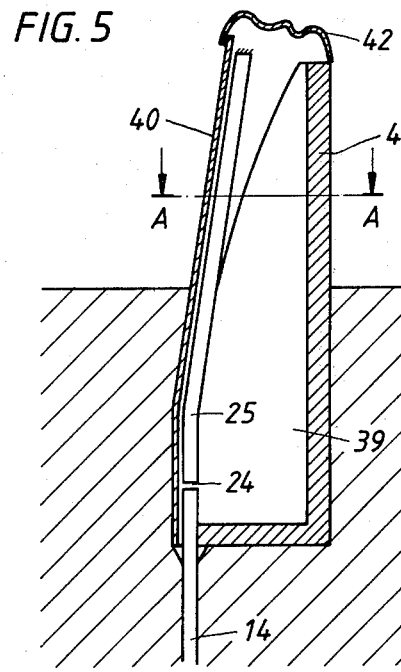
FIG.5a
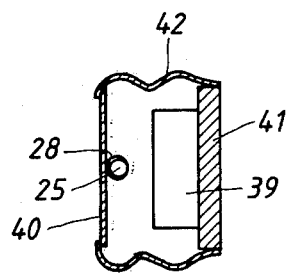

FIBER OPTICAL MEASURING DEVICE

BACKGROUND

Field of the Invention

The present invention relates to fiber optical measuring devices for measuring physical parameters of a medium, such as the level of the medium, and in particular to such devices using an electronic unit and a transducer unit interconnected by at least one optical fiber, the transducer including at least one light guide coupled to the optical fiber for transmitting signals representative of the physical parameter being measured with the light guide at least partially immersed in the medium.

In, for example, the petroleum and the petrochemical industries, there is a considerable need to measure fluid levels. The environment at the point of measurement is often of such a nature that the risk of explosion is very great, and the present invention is primarily intended to eliminate the risk of electrical energy from the transducer setting fire to the surrounding medium.

SUMMARY OF THE INVENTION

The invention is characterized in that a light guide is adapted to be at least partially immersed into or introduced into the medium, the level or other parameters of which is to be measured. The light guide consists of a core having a higher refractive index than a surrounding sheath. The sheath has one or several uncovered regions along the light guide or regions that are only very thinly covered, i.e., transparent regions. When the guide is immersed into the medium, the medium influences the guide such that light in the thinly covered or uncovered regions of the guide is transmitted from the core. The light transmission characteristics of the immersed portion of the guide is adapted to be so changed by the surrounding medium that light in the thinly covered or uncovered regions of the guide is transmitted from the core at the immersed portion of the guide. The transmission of light is adapted to be accomplished by bringing a light guiding or light-absorbing structure into optical contact with the core in the light transparent regions by means of the medium, or alternatively that the transmission of light is adapted to be accomplished by bringing the medium into optical contact with the core in the light transparent regions. This gives an accurately measured value of, for example, the level of the medium. The degree of contact thus determines the measured value, and an accurate indication of the level may be obtained.

BRIEF DESCRIPTION OF THE DRAWINGS

The aforementioned objects, features and advantages of the invention are apparent from the accompanying Figures, wherein:

FIG. 1 shows an embodiment of the transducer unit and the electronic unit;

FIG. 1a shows the transducer in cross-section along line A—A of FIG. 1, and FIG. 1b is a cross-section along line B—B of FIG. 1;

FIG. 2 shows an optical fiber surrounded by a coil and FIGS. 2a and 2b are respective cross-sections along lines A—A and B—B of FIG. 2, respectively;

FIG. 3 shows an optical fiber wound as a coil;

FIG. 4 shows a sheathed fiber;

FIG. 5 shows a level transducer in which the optical fiber is fixed to a movable membrane; and FIG. 5a is a section along line A—A in FIG. 5.

DETAILED DESCRIPTION OF THE PREFERRED EMBODIMENTS

FIG. 1 shows an exemplary embodiment of fiber optical transducer unit G and electronic unit E. In the example shown, transducer unit G consists of a level transducer connected to electronic unit E by optical fiber 14. Light from light-emitting diode or laser diode 1, having a maximum emission at wavelength $\lambda_1$, is coupled via optical fiber 8, branch 10, optical fiber 11, branch 13 and optical fiber 14 to interference filter 24. Interference filter 24 is designed so that the main portion of the light from diode 1 (around $\lambda_1$) will be reflected and, after passage through optical fiber 14, branch 13 and optical fiber 12, to emit a light signal to photodiode or photo-transistor 15, which signal is utilized as a reference signal. The light from light-emitting or laser diode 2 with a wavelength range around $\lambda_2$ is supplied via light fiber 9, branch 10, light fiber 11 and branch 13 as well as light fiber 14 to interference filter 24. Interference filter 14 is designed so that the main portion of the light signal ranging around $\lambda_2$ is transmitted through the filter. This light therefore reaches transducer G, and after reflection by optical fiber 30, is transmitted through interference filter 24, optical fiber 14, branch 13 and optical fiber 12, a measuring signal arrives at photo-detector 15. Light sources 1 and 2 are driven alternately by drive circuits 3 and 4, respectively, and voltage source 20 ($V_{ref}$) being alternately coupled to drive circuits 3 and 4 by means of switch 17. Oscillator 19, which controls switch 17, also synchronously controls the switch 18, which alternately couples the detector signal, amplified by amplifier 16, to sample and hold circuits 21 and 22. Sample and hold circuit 21 operates on the reference signal and sample and hold circuit 22 operates on the measuring signal. By forming a quotient in quotient forming means 23, measuring signal U is obtained which is compensated for drift and instabilities by the optoelectronics and the fiber optics. To ensure the constant distribution of the emission spectra in light sources 1 and 2, they are temperature-controlled by controllers 5 and 6, respectively, which are in turn controlled by control unit 7. Controllers 5 and 6 may either be Peltier elements or simple heat sources, in both cases containing temperature sensors.

Level transducer G is immersed into medium 31 and is intended to measure the level thereof in vessel 32. Because of the natural weight of medium 31, light-conducting plastic film 26 is pressed against optical fiber 25, which has been lowered below the surface of medium 31. Because film 26 has a higher refractive index than sheath 28 of optical fiber 25 and because that optical fiber 25 has no sheath or only a very thin sheath at the point where plastic film 26 makes contact with optical fiber 25, light will be transmitted from the optical fiber and to plastic film 26 below the surface of medium 31 with the result that the light losses in optical fiber 25 increase with the level of the medium and the measuring signal decreases correspondingly. Optical fiber 25 is mounted in casing 29 and plastic film 26 is attached on the inside of membrane 27, which is stretched out on casing 29, as shown by the cross-section FIGS. 1a and 1b. FIG. 1a shows a cross-section of the transducer at the section A—A of FIG. 1, which is located above the surface of the medium 31 (see FIG. 1). Optical fiber 25 is attached to casing 29 by glue 33, the casing also supporting membrane 27 on which plastic film 26 is attached. In front of plastic film 26 there is an air gap to optical fiber 25, the core of the fiber then being exposed over distance 34, the so-called special region, where sheath 28 has thus been removed or has been made extremely thin so as to be transparent. Below the surface of medium 31 membrane 27 is pressed in against optical fiber 25 according to FIG. 1b. This results in a well-defined contact surface between plastic film 26 and optical fiber 25 at the opening 34 of sheath 28 (See FIG. 1a).

The advantage of using light-conducting plastic film 26 is that a well-defined transmission of light may be obtained. Of course, light may also be transmitted directly to an absorber which is pressed against the optical fiber at 34, which involves the advantage that membrane 27 may be used directly for the transmission of light. If plastic film 26 is provided with an interference layer having the same reflecting spectrum as filter 24, the filter may be eliminated as the reference signal in that case is generated by plastic film 26 itself. The level measured will thus become dependent on how large a portion of, for example, film 26 that is pressed against the core of optical fiber 25 at special region 34. A measuring signal representative of the level can then be easily obtained by quotient forming means 23 in a manner well known to those skilled in the art.

In the modified embodiment of the transducer unit as shown in FIGS. 2, 2a and 2b, optical fiber 25 is surrounded by wire-wound coil 35, which is coated on the outside with membrane 27. Above the surface of the medium 31 there exists an air gap between coil 35 and exposed portion 34 of the core of optical fiber 25, whereas the pressure of medium 31 below the surface thereof provides optical contact between coil 35 and special exposed region 34, which in turn means that light is transmitted from optical fiber 25. Light passing into the transducer will thus to a varying extent be transmitted in dependence on the level of medium 31 into which optical fiber 25 has been inserted or immersed. Instead of winding coil 35 around optical fiber 25, optical fiber 25 may itself be wound as a coil according to the further modified embodiment of FIG. 3. Optical fiber 25 is wound on drum 37, which is provided with bottom plate 37a and coil strips 36 for retaining cylindrical membrane 27. Below the surface of medium 31, membrane 27 is pressed against the end of optical fiber 30, thus increasing the fiber damping.

In all the proposals for transducers described above, the air gap between the optical fiber and the structure, from which the light is transmitted, may be provided with a liquid having somewhat lower refractive index than the core of the optical fiber. Of course, medium 31, the level of which is to be measured, may also be used for transmitting light from optical fiber 25. However, the light transmission will then be very great, resulting in a very small measuring range. To increase the measuring range, however, the evanescent waves in a sheathed optical fiber may be used according to the modified transducer embodiment of FIG. 4. In that case, however, sheath 38 must be so thin that the evanescent waves therein are not negligible at the surface of the sheath.

Finally, FIGS. 5 and 5a show a level measuring transducer in which optical fiber 25 is attached to movable membrane 40 instead of light-coupling structure 39. Optical fiber 14 enters the transducer from the bottom thereof, and medium 31 presses flexible plate 40 and optical fiber 25 against slightly curved glass prism 39. As is shown in FIG. 5a, fiber sheath 28 is exposed at that part thereof facing prism 39, so light can be transmitted from optical fiber 25 to prism 39 when optical fiber 25 is pressed against it. The transducer is held tight with the aid of membrane 42, but which permits the necessary movements of membrane 40 and optical fiber 25.

It will be apparent to those skilled in the art that there are many variations of both the transducer and electronic processing unit that fall within the structure and function thereof as set forth in the exemplary embodiments described herein.

What is claimed is:

1. A transducer for a fiber optical measuring device for the measurement of physical parameters of a medium, comprising:
    at least one light guide for receiving light signals and transmitting output light signals representative of the parameter of said medium being measured and adapted to be partially immersed into said medium;
    a sheath surrounding said light guide and including at least one transparent region thereof;
    said light guide further including a core having a higher refractive index than said sheath;
    said core transmitting light from said at least one transparent region at the immersed portion of said light guide to produce said output light signals; and
    light transmission varying means spaced from said light guide and being brought into optical contact with said core by immersion of said light guide into said medium such that the light transmitted from said at least one transparent region is altered by said medium.

2. A transducer as in claim 1 wherein said medium is in optical contact with said core in said at least one transparent region immersed within said medium.

3. A transducer as in claim 1 wherein said light transmission varying means has a refractive index greater than or equal to the refractive index of said core.

4. A transducer as in claim 3 wherein said light transmission varying means is a resilient membrane adapted to be pressed against said core by immersion of said light guide into said medium at clearly defined portions of said core.

5. A transducer as in claim 1 wherein said light transmission varing means includes surface portions providing a plurality of well-defined contact points with said core upon immersion of said light guide in said medium.

6. A transducer as in claim 5 wherein said light transmission varying means is a wire coil wound around the core of said light guide.

7. A transducer as in claim 5 wherein said light transmission varying means is a corrugated light conductor surrounding the core of said light guide.

8. A transducer as in claim 1 wherein said light transmission varying means includes a surface curving along the longitudinal axis of the light guide, said light guide being partially bent along said curved surface by said medium upon immersion of said light guide therein.

9. A transducer as in claim 1 wherein said light guide is an optical fiber.

10. A transducer as in claim 9 wherein said optical fiber is wound in the form of a helical coil.

11. A transducer as in claim 1 wherein said light transmission varying means is spaced from said core, and the space between said core and said light transmission varying means includes a liquid having a well-defined refractive index.

12. A transducer as in claim 1 further comprising an interference filter at the end of said at least one light guide receiving light signals.

13. A fiber optical measuring device using the transducer as in claim 1 and further comprising:
   means for generating light signals having first and second different wavelengths;
   optical fiber means for transmitting said generated light to said at least one light guide;
   interference filter means for reflecting at least a portion of said light signals at the end of said at least one light guide;
   said optical fiber means including an optical fiber for transmitting said output light signals;
   means for detecting said output light signals from said fiber optical means; and
   means for processing the detected signals to generate a signal representative of the physical parameter of said medium.

14. The fiber optical measuring device as in claim 13 further comprising means for alternately periodically generating light signals of said first and second wavelengths.

15. A fiber optical measuring device as in claim 14 further including means for temperature stabilizing said means for generating light signals.

16. A fiber optical measuring device as in claim 14 wherein said means for processing includes first and second sample and hold circuits each having an input controlled in synchronization with the operation of said means for periodically and alternately generating said light signals to alternately input the output of said light detecting means, and means for dividing the respective outputs of said first and second sample and hold circuits for generating a signal representing the measured physical parameters of the medium.

* * * * *